United States Patent
Lv

(10) Patent No.: US 11,539,209 B2
(45) Date of Patent: Dec. 27, 2022

(54) CONTROL CIRCUIT FOR WEARABLE DEVICE, WEARABLE DEVICE

(71) Applicant: BOE TECHNOLOGY GROUP CO., LTD., Beijing (CN)

(72) Inventor: Zhendong Lv, Beijing (CN)

(73) Assignee: BEIJING BOE TECHNOLOGY DEVELOPMENT CO., LTD., Beijing (CN)

( * ) Notice: Subject to any disclaimer, the term of this patent is extended or adjusted under 35 U.S.C. 154(b) by 348 days.

(21) Appl. No.: 16/925,370

(22) Filed: Jul. 10, 2020

(65) Prior Publication Data

US 2021/0013715 A1 Jan. 14, 2021

(30) Foreign Application Priority Data

Jul. 11, 2019 (CN) .......................... 201921086210.1

(51) Int. Cl.
*H02J 3/00* (2006.01)
*H03K 5/24* (2006.01)
(Continued)

(52) U.S. Cl.
CPC .............. *H02J 3/00* (2013.01); *A61B 5/0022* (2013.01); *A61B 5/08* (2013.01); *A61B 5/1118* (2013.01);
(Continued)

(58) Field of Classification Search
CPC ...... H02M 3/158; H02M 3/07; H02M 1/0058; H02M 1/0009; H02M 3/33507; H02M 3/1584; H02M 3/1582; H02M 3/156; H03G 1/0088; G05F 1/63; A61B 5/0022; A61B 5/08; A61B 5/1118; A61B 5/25; A61B 5/4806; A61B 2560/0214
See application file for complete search history.

(56) References Cited

U.S. PATENT DOCUMENTS 6,064,239 A * 5/2000 Matsuoka ............ H03K 5/2481
327/78
6,559,688 B2 * 5/2003 Ohkido ..................... H03F 3/72
327/69
(Continued)

FOREIGN PATENT DOCUMENTS

CN 104873188 9/2015
CN 205126227 4/2016

*Primary Examiner* — John W Poos
(74) *Attorney, Agent, or Firm* — Calfee, Halter & Griswold LLP

(57) ABSTRACT

A control circuit for a wearable device includes: a power supply circuit, a DC blocking circuit, and a voltage comparison circuit. The power supply circuit is connected to a high voltage end, a low voltage end, a first signal input end, a second signal input end; the DC blocking circuit is connected to the first node, the second node, and a sensor in the wearable device; the voltage comparison circuit is connected to the first node, a reference voltage end and an output end, and configured to compare voltages of the first node and the reference voltage end; and output a first control signal through the output end when the voltage of the first node is smaller than the voltage of the reference voltage end, and output a second control signal through the output end when the voltage of the first node is larger than the voltage of the reference voltage end.

16 Claims, 4 Drawing Sheets

(51) Int. Cl.
*G06F 1/32* (2019.01)
*A61B 5/00* (2006.01)
*A61B 5/08* (2006.01)
*A61B 5/11* (2006.01)
*A61B 5/25* (2021.01)

(52) U.S. Cl.
CPC .............. *A61B 5/25* (2021.01); *A61B 5/4806* (2013.01); *G06F 1/32* (2013.01); *H03K 5/24* (2013.01); *A61B 2560/0214* (2013.01)

(56) References Cited

U.S. PATENT DOCUMENTS

| | | | |
|---|---|---|---|
| 7,755,400 B2 * | 7/2010 | Jordanger | H04L 25/4902 |
| | | | 327/531 |
| 8,890,565 B2 * | 11/2014 | Honda | H03K 19/018521 |
| | | | 326/82 |
| 8,896,377 B1 * | 11/2014 | Shrestha | H03F 3/45071 |
| | | | 381/120 |
| 2016/0038055 A1 * | 2/2016 | Wheeler | A61B 5/7225 |
| | | | 600/301 |
| 2020/0264225 A1 * | 8/2020 | Kobayashi | G01R 29/26 |
| 2020/0393706 A1 * | 12/2020 | Vera Villarroel | H03F 3/45973 |

* cited by examiner

CONTROL CIRCUIT FOR WEARABLE DEVICE, WEARABLE DEVICE

The present application is based on and claims the priority to the Chinese Patent Application No. 201921086210.1, filed on Jul. 11, 2019, the entire contents of which are hereby incorporated by reference.

TECHNICAL FIELD

The present disclosure relates to the field of electronic technology, in particular to a control circuit for a wearable device and a wearable device.

BACKGROUND

With continuous acceleration of life rhythm, people's pressure is increasing constantly. Most people have different levels of heart problems, sleep problems, etc., thus generating wearable devices for monitoring physical health.

However, wearable devices in the related art are provided with a power switch. Users need to manually operate the power switch to switch on and off, which is very inconvenient to use.

SUMMARY

The embodiments of the present disclosure provide a control circuit for a wearable device and a wearable device, which can realize automatic switching on and off and avoid accidental start-up.

To achieve the above purpose, embodiments of the present disclosure adopt following technical solutions.

In an aspect, an embodiment of the present disclosure provides a control circuit for a wearable device, including: a power supply circuit, a DC blocking circuit, and a voltage comparison circuit, wherein the power supply circuit is connected to a high voltage end, a low voltage end, a first signal input end, a second signal input end, a first node and a second node; the power supply circuit is configured to output a voltage of the first signal input end to the first node and output a voltage of the second signal input end to the second node according to voltages supplied by the high voltage end and the low voltage end; the DC blocking circuit is connected to the first node, the second node, and a sensor in the wearable device, and configured to block DC signals on the first node and the second node from flowing to the sensor, and cause AC signals on the first node and the second node to flow to the sensor; the voltage comparison circuit is connected to the first node, a reference voltage end and an output end, and configured to compare voltages of the first node and the reference voltage end; and output a first control signal through the output end when the voltage of the first node is smaller than the voltage of the reference voltage end, and output a second control signal through the output end when the voltage of the first node is larger than the voltage of the reference voltage end.

Optionally, the power supply circuit includes a first power supply sub-circuit and a second power supply sub-circuit; the first power supply circuit is connected to the high voltage end, the first signal input end and the first node; the second power supply circuit is connected to the low voltage end, the second signal input end and the second node.

Optionally, the DC blocking circuit includes a first DC blocking sub-circuit and a second DC blocking sub-circuit; the first DC blocking sub-circuit is connected to the first node and the sensor; the second DC blocking sub-circuit is connected to the second node and the sensor.

Optionally, the first power supply sub-circuit includes a first resistor, and the second power supply sub-circuit includes a second resistor; a first end of the first resistor is connected to the high voltage end, and a second end of the first resistor is connected to the first node and the first signal input end; a first end of the second resistor is connected to the low voltage end, and a second end of the second resistor is connected to the second node and the second signal input end.

Optionally, the first DC blocking sub-circuit includes a first capacitor, and the second DC blocking sub-circuit includes a second capacitor; a first end of the first capacitor is connected to the first node, and a second end of the first capacitor is connected to the sensor; a first end of the second capacitor is connected to the first node, and a second end of the second capacitor is connected to the sensor.

Optionally, the control circuit further includes a voltage follower, wherein an input end of the voltage follower is connected to the first node, and an output end of the voltage follower is connected to the voltage comparison circuit and configured to amplify a DC signal on the first node and keep the voltage unchanged.

Optionally, the sensor is configured to collect at least one of electrocardiogram data, respiratory data, sleep data, and exercise data.

In another aspect, an embodiment of the present disclosure provides a wearable device, including the control circuit for a wearable device described above, a communication module, and a power management module, wherein an output end of the voltage comparison circuit in the control circuit is connected to a power management module, and the power management module is connected to the communication module; the power management module is configured to convert the communication module from a sleep state to an operating state according to the first control signal output by the voltage comparison circuit; and further configured to convert the communication module from the operating state to the sleep state according to the second control signal output by the voltage comparison circuit.

Optionally, the wearable device further includes a processor and a memory, wherein the processor is configured to receive data collected by the sensor and store the data in the memory.

Optionally, the communication module is a Bluetooth module or a Wi-Fi module or a Zigbee module.

The present disclosure provides a control circuit for a wearable device and a wearable device. A voltage of the first signal input end is output to the first node and a voltage of the second signal input end is output to the second node through a power supply circuit connected to a high voltage end, a low voltage end, a first signal input end, a second signal input end, a first node and a second node. Then, a voltage comparison circuit compares voltages of the first node and the reference voltage end, and correspondingly outputs a control signal or a second control signal to automatically control on and off of the wearable device. Meanwhile, the DC blocking circuit makes AC signals on the first node and the second node flow to the sensor and blocks DC signals on the first node and the second node from flowing to the sensor, so that the sensor can work normally while avoiding internal impedance of the sensor from forming a loop to cause accidental start-up of the wearable device.

BRIEF DESCRIPTION OF THE DRAWINGS

In order to more clearly explain technical solutions in the embodiments of the present disclosure or in the prior art, drawings required for describing the embodiments or the prior art will be briefly introduced in the following. Obviously, the drawings in the following description are only some embodiments of the present disclosure. Other drawings can also be obtained based on these drawings for those skilled in the art, without paying any creative labor.

REFERENCE NUMERALS

1—control circuit; 10—power supply circuit; 20—DC blocking circuit; 30—voltage comparison circuit; 40—sensor; 50—voltage follower; 60—communication module; 70—power management module; 80—processor; 90—memory; 101—first power supply sub-circuit; 102—second power supply sub-circuit; 201—first DC blocking circuit; 202—second DC blocking circuit.

DETAILED DESCRIPTION

The technical solutions in the embodiments of the present disclosure will be described clearly and completely in conjunction with the drawings in the embodiments of the present disclosure. Obviously, the described embodiments are only a part of the embodiments of the present disclosure, but not all embodiments. The embodiments used in the present disclosure and all other embodiments obtained by those skilled in the art without creative work all fall within the protection scope of the present disclosure.

Figure 1:
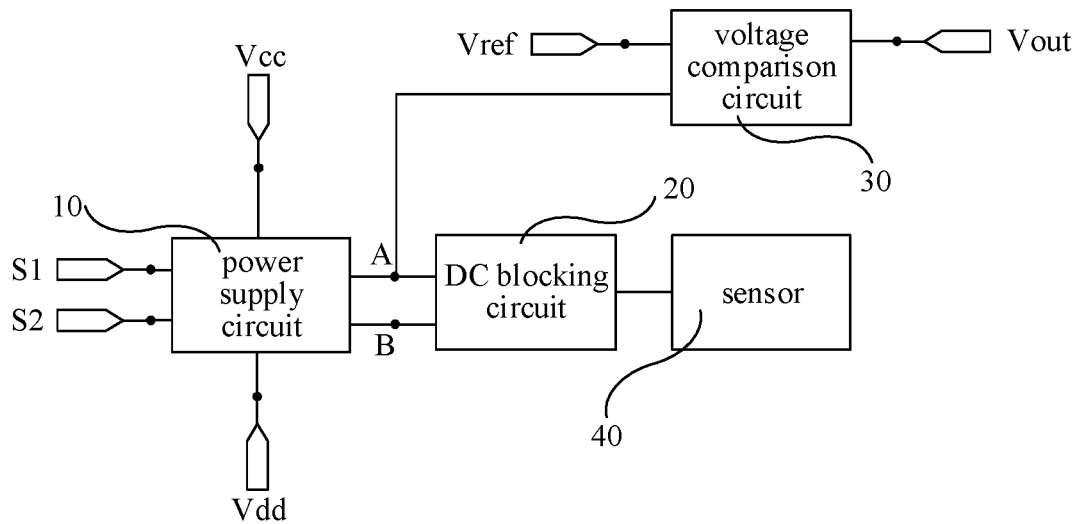
FIG. 1 is a schematic diagram of a control circuit for a wearable device provided by an embodiment of the present disclosure.

An embodiment of the present disclosure provides a control circuit for a wearable device. As shown in FIG. 1, the control circuit includes: a power supply circuit 10, a DC blocking circuit 20, and a voltage comparison circuit 30.

The power supply circuit 10 is connected to a high voltage end Vcc, a low voltage end Vdd, a first signal input end S1, a second signal input end S2, a first node A and a second node B. The power supply circuit 10 is configured to output a voltage of the first signal input end S1 to the first node A and output a voltage of the second signal input end S2 to the second node B according to voltages supplied by the high voltage end Vcc and the low voltage end Vdd.

The DC blocking circuit 20 is connected to the first node A, the second node B, and a sensor 40 in the wearable device, and configured to block DC signals on the first node A and the second node B from flowing to the sensor 40, and cause AC signals on the first node A and the second node B to flow to the sensor 40.

The voltage comparison circuit 30 is connected to the first node A, a reference voltage end Vref and an output end Vout, and configured to compare voltages of the first node A and the reference voltage end Vref. A first control signal is output through the output end Vout when the voltage of the first node A is smaller than the voltage of the reference voltage end Vref, and a second control signal is output through the output end Vout when the voltage of the first node A is larger than the voltage of the reference voltage end Vref.

In the embodiment, the first control signal is a low level, and the second control signal is a high level. Herein, "high" and "low" only represent a relative magnitude relationship of input voltages.

In some embodiments, the voltage comparison circuit 30 may generally adopt, for example, the TS881 chip of ST Company, the MAX9060 chip of MAXIM Company, or the like. An operating current of these chips is about 1 μA. Depending on different chip manufacturers, the operating current of the chip is somewhat different.

In some embodiments, there is a plurality of sensors 40.

The present disclosure provides a control circuit for a wearable device. A voltage of the first signal input end S1 is output to the first node A and a voltage of the second signal input end S2 is output to the second node B through a power supply circuit 10 connected to a high voltage end Vcc, a low voltage end Vdd, a first signal input end S1, a second signal input end S2, a first node A and a second node B. Then, a voltage comparison circuit 30 compares voltages of the first node A and the reference voltage end Vref, and correspondingly outputs a control signal or a second control signal to automatically control on and off of the wearable device. Meanwhile, the DC blocking circuit 20 makes AC signals on the first node A and the second node B flow to the sensor 40 and blocks DC signals on the first node A and the second node B from flowing to the sensor 40, so that the sensor 40 can work normally while avoiding internal impedance of the sensor 40 from forming a loop to cause accidental start-up of the wearable device.

Figure 2:
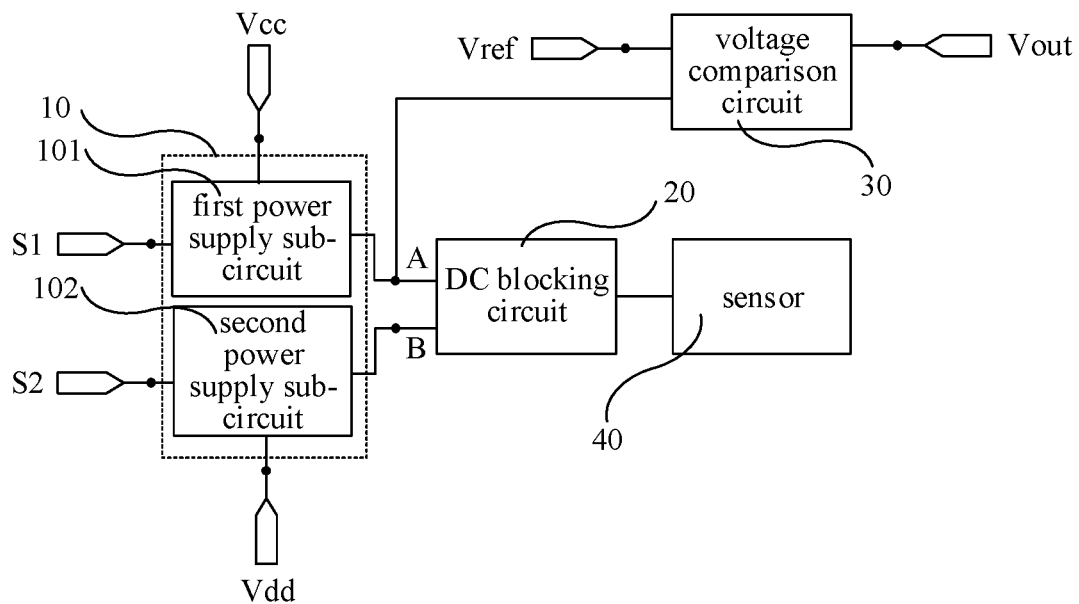
FIG. 2 is a schematic diagram of a control circuit for a wearable device provided by another embodiment of the present disclosure.

Optionally, as shown in FIG. 2, the power supply circuit 10 includes a first power supply sub-circuit 101 and a second power supply sub-circuit 102.

The first power supply circuit 101 is connected to the high voltage end Vcc, the first signal input end S1 and the first node A. The second power supply circuit 102 is connected to the low voltage end Vdd, the second signal input end S2 and the second node B.

Figure 3:
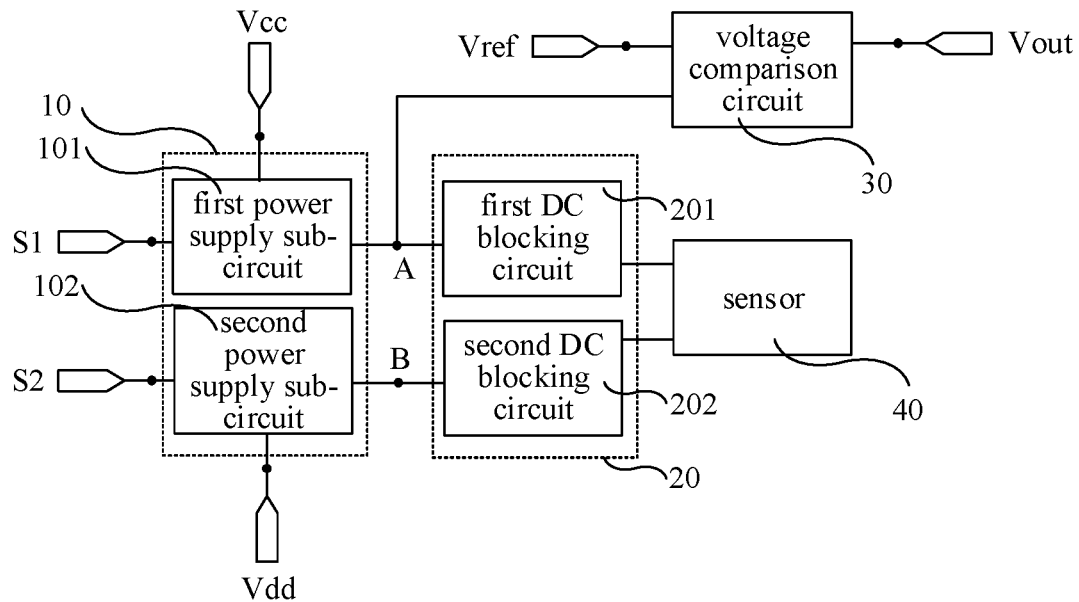
FIG. 3 is a schematic diagram of a control circuit for a wearable device provided by yet another embodiment of the present disclosure.

Optionally, as shown in FIG. 3, the DC blocking circuit 30 includes a first DC blocking sub-circuit 201 and a second DC blocking sub-circuit 202.

The first DC blocking sub-circuit 201 is connected to the first node A and the sensor 40. The second DC blocking sub-circuit 202 is connected to the second node B and the sensor 40.

Figure 4:
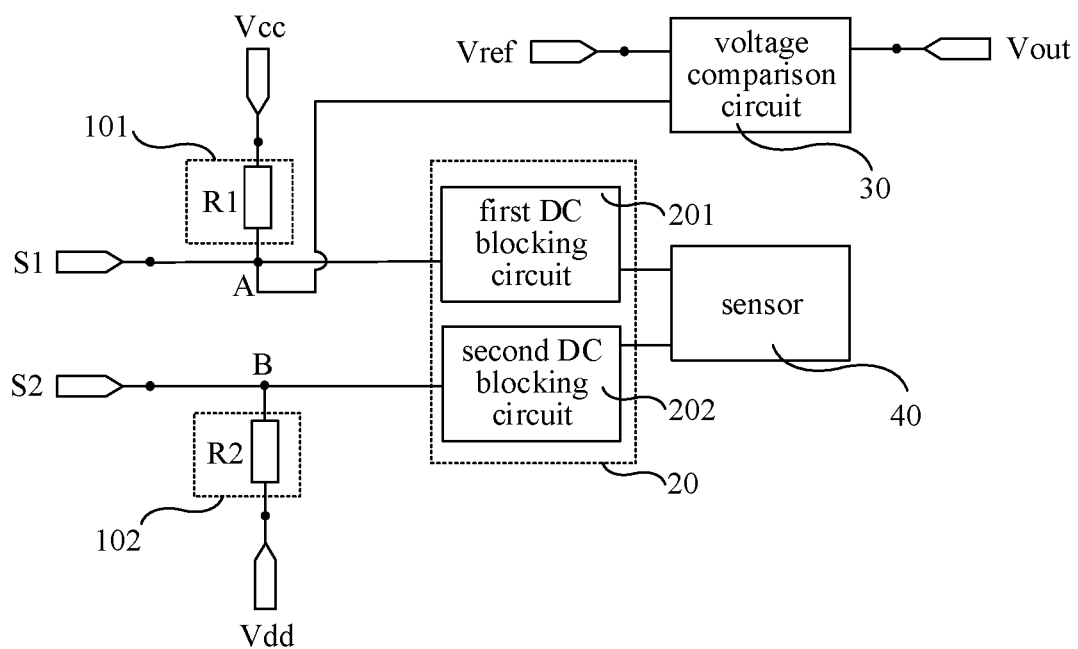
FIG. 4 is a schematic diagram of a control circuit for a wearable device provided by yet another embodiment of the present disclosure.

Optionally, as shown in FIG. 4, the first power supply sub-circuit 101 includes a first resistor R1, and the second power supply sub-circuit 102 includes a second resistor R2.

A first end of the first resistor R1 is connected to the high voltage end Vcc, and a second end of the first resistor R1 is connected to the first node A and the first signal input end S1. A first end of the second resistor R2 is connected to the low voltage end Vdd, and a second end of the second resistor R2 is connected to the second node B and the second signal input end S2.

It should be noted that the first power supply circuit 101 may further include a plurality of resistors connected in parallel, and the second power supply circuit 102 may also include a plurality of resistors connected in parallel. The above is only an example of the first power supply circuit 101 and the second power supply circuit 102. Other structures with the same functions as the first power supply circuit 101 and the second power supply circuit 102 all should belong to the protection scope of the present disclosure, which will not be repeated herein.

Figure 5:
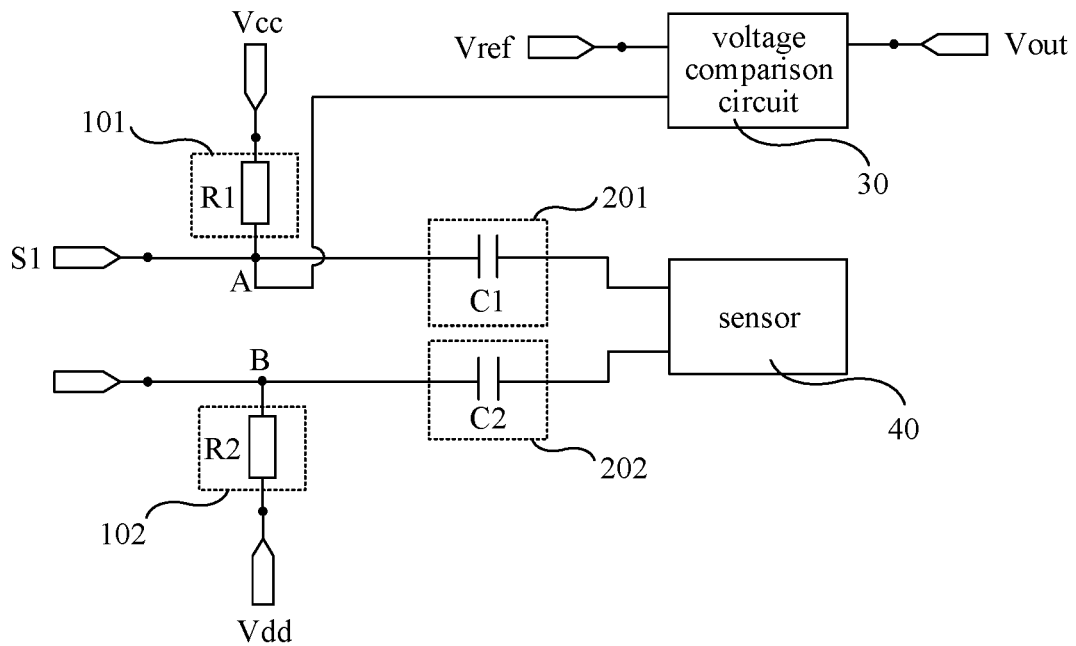
FIG. 5 is a schematic diagram of a control circuit for a wearable device provided by yet another embodiment of the present disclosure.

Optionally, as shown in FIG. 5, the first DC blocking sub-circuit 201 includes a first capacitor C1, and the second DC blocking sub-circuit 201 includes a second capacitor C2.

A first end of the first capacitor C1 is connected to the first node A, and a second end of the first capacitor C1 is connected to the sensor 40. A first end of the second capacitor C2 is connected to the second node B, and a second end of the second capacitor C2 is connected to the sensor 40.

It should be noted that the first power supply circuit 201 may further include a plurality of capacitors C1 connected in parallel, and the second power supply circuit 202 may also include a plurality of capacitors C2 connected in parallel. The above is only an example of the first power supply circuit 201 and the second power supply circuit 202. Other structures with the same functions as the first power supply circuit 201 and the second power supply circuit 202 all should belong to the protection scope of the present disclosure, which will not be repeated herein.

Figure 6:
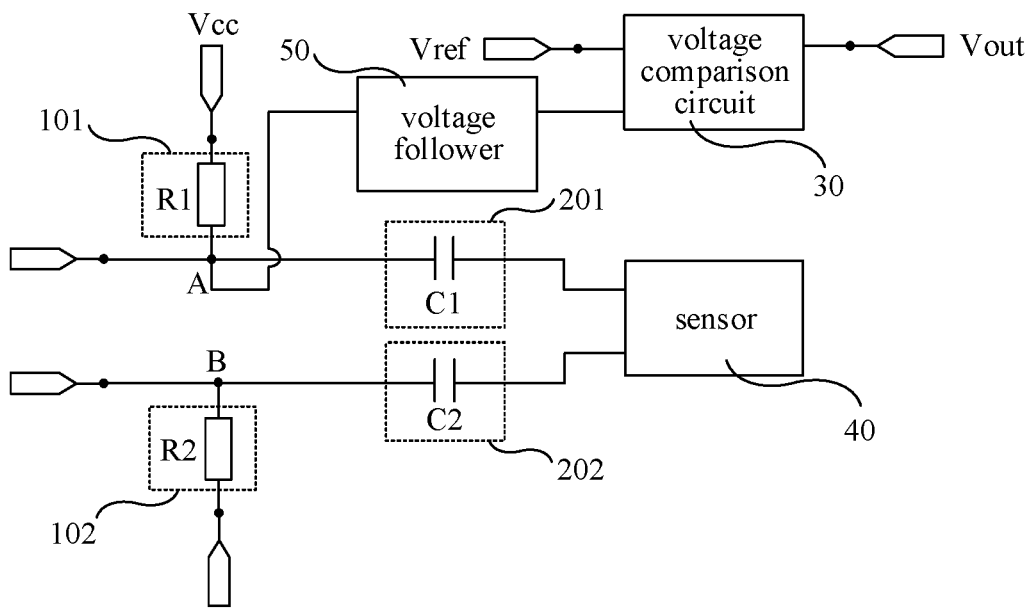
FIG. 6 is a schematic diagram of a control circuit for a wearable device provided by yet another embodiment of the present disclosure.

Optionally, as shown in FIG. 6, the control circuit for a wearable device further includes a voltage follower 50. An input end of the voltage follower 50 is connected to the first node A, and an output end of the voltage follower 50 is connected to the voltage comparison circuit 30 and configured to amplify a DC signal on the first node A and keep the voltage unchanged.

In the embodiment, the voltage follower 50 has characteristics of high input impedance and low output impedance, and has functions of buffering and isolation, so that front and rear stage circuits connected with the voltage follower 50 do not affect each other.

In some embodiments, the voltage follower 50 may adopt an LM324 chip, an LM358 chip, or the like.

Optionally, the sensor 40 is used to collect at least one of electrocardiogram data, respiratory data, sleep data, and exercise data.

For example, the sensor 40 may be an electrocardiogram sensor, a motion sensor, a respiration sensor, or the like.

For example, the sensor 40 for collecting electrocardiogram data and respiratory data is an electrocardiogram respiration simulation front end, such as ADS1292R, ADAS1000 of the company Ti, or the like. The motion sensor may be, for example, a three-axis or six-axis sensor widely used in mobile phones and tablet computers.

Figure 7:
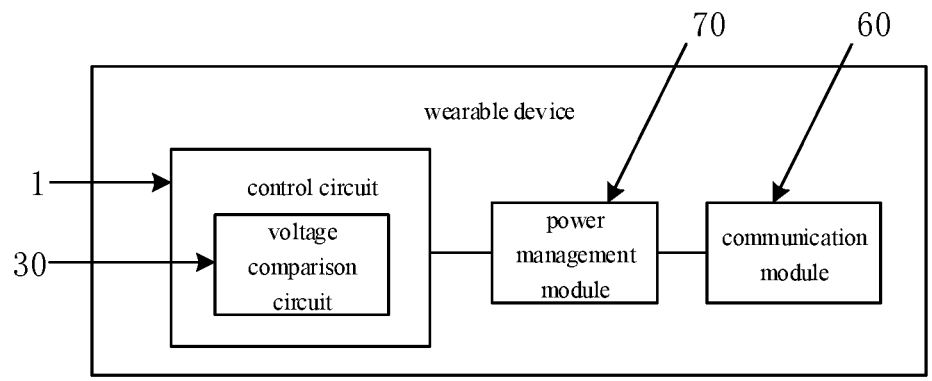
FIG. 7 is a schematic diagram of a wearable device provided by an embodiment of the present disclosure.

An embodiment of the present disclosure further provides a wearable device, as shown in FIG. 7, including the control circuit 1 for a wearable device described above, a communication module 60, and a power management module 70.

An output end of the voltage comparison circuit 30 in the control circuit 1 is connected to a power management module 70, and the power management module 70 is connected to the communication module 60.

The power management module 70 is configured to convert the communication module 60 from a sleep state to an operating state according to the first control signal output by the voltage comparison circuit 30; and further configured to convert the communication module 60 from the operating state to the sleep state according to the second control signal output by the voltage comparison circuit 30.

The power management module 70 may be a power management module 70 for wearable devices or smart portable devices supplied by companies such as Ti, ADI, and Amerson.

The communication module 60 is used to enable the wearable device to communicate with an external terminal, such as a mobile phone. For example, the communication module 60 may be a Bluetooth module of a smart bracelet.

It should be noted that when the first signal input end and the second signal input end in the control circuit 1 contact the human body, the human body is equivalent to a resistance of 1 M~10 M. At this time, the voltage at the first node is a low level, and the voltage is transmitted to the voltage comparison circuit 30 via the voltage follower 50. The low level is smaller than the voltage of the reference voltage end. Therefore, the voltage comparison circuit 30 outputs the first control signal as a low level, so that the power management module 70 makes the communication module 60 convert from the sleep state to the operating state based on the low level.

When the first signal input end and the second signal input end in the control circuit 1 do not contact with the human body, the human body is equivalent to an infinite resistance. At this time, the voltage at the first node is a high level, and the voltage is transmitted to the voltage comparison circuit 30 via the voltage follower 50. The high level is greater than the voltage of the reference voltage end. Therefore, the voltage comparison circuit 30 outputs the second control signal, which is a high level, so that the power management module 70 makes the communication module 60 convert from the operating state to the sleep state according to the high level.

It can be understood that, as for the communication module 60, the control circuit 1 is in an operating state only when the first signal input end and the second signal input end in the control circuit 1 contact the human body, and it is in a low power consumption state at other time.

Figure 8:
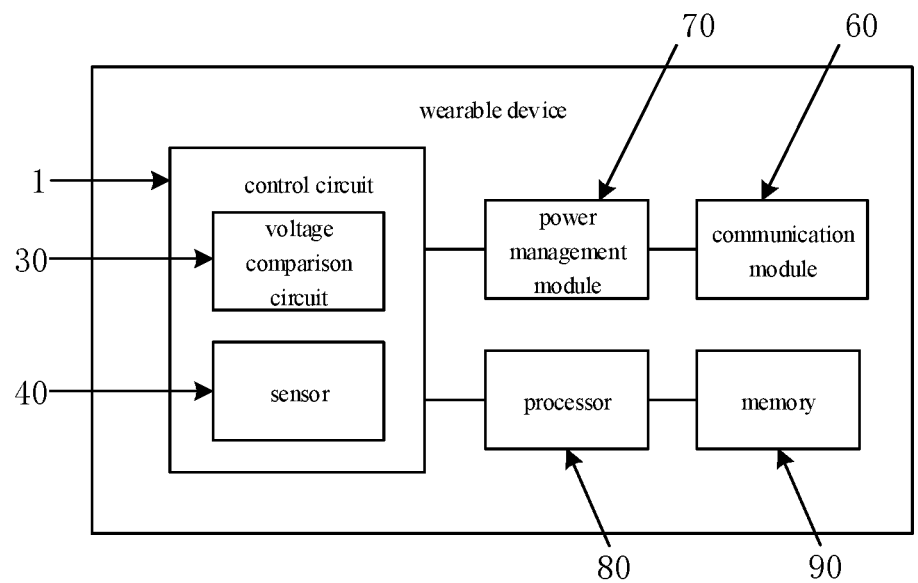
FIG. 8 is a schematic diagram of a wearable device provided by another embodiment of the present disclosure.

Optionally, as shown in FIG. 8, the wearable device further includes a processor 80 and a memory 90.

The processor 80 is used to receive data collected by the sensor 40 and store the data in the memory 90.

In the embodiment, the data detected by the sensor 40 of the wearable device may be sign data, such as at least one of electrocardiogram data, respiratory data, sleep data, and exercise data, of a detected object, for example, a person. The data detected by the sensor 40 of the wearable device may also be environmental data, such as ultraviolet intensity, temperature, altitude, etc. of a detected object, for example, a person. The required data can be detected by integrating the corresponding sensor 40 in the wearable device.

The detected data may further include data of the wearable device itself, such as time and power or the like, although not explicitly described.

The processor 80 may be a central processing unit CPU (such as ARM Cortex-M3), a digital signal processor DSP (such as CEVA DSP), a single-chip MCU (such as STM32, MSP430), and so on.

The memory 90 may be a Flash memory, a solid state drive, a CF card, a MicroSD card, an SD card, eMMC, or the like.

Optionally, the communication module 60 includes one or more of a Bluetooth module, a Wi-Fi module, and a Zigbee module.

For example, the Bluetooth modules is CC2541, CC2640, SKB369, RF-BM-SOA, or the like; the Wi-Fi module is Ti's CC3100, Marvell's MW300, Broadcom's BCM4390, MTK's MT7688, or the like; the Zigbee module is NXP's JN5169, Ti's CC2530, or the like.

The present disclosure provides a wearable device. By inputting the first control signal and the second control signal output from the voltage comparison circuit 30 in the control circuit 1 to the power management module 70, the power management module 70 can control the communication module 60 to convert between the operating state and the sleep state, so as to achieve automatic switching on and off.

The above is only specific implementation of the present disclosure, but the protection scope of the present disclosure is not limited to this. Any change or substitute easily conceived by any person skilled in the art within the technical scope disclosed by the present disclosure should be covered within the protection scope of the present disclosure. Therefore, the protection scope of the present disclosure shall be subject to the protection scope of the claims.

What is claimed is:

1. A control circuit for a wearable device, comprising: a power supply circuit, a DC blocking circuit, and a voltage comparison circuit,
   wherein the power supply circuit is connected to a high voltage end, a low voltage end, a first signal input end, a second signal input end, a first node, and a second node; the power supply circuit is configured to output a voltage of the first signal input end to the first node and to output a voltage of the second signal input end to the second node according to voltages supplied by the high voltage end and the low voltage end;
   the DC blocking circuit is connected to the first node, the second node, and a sensor in the wearable device, and is configured to block DC signals on the first node and the second node from flowing to the sensor, and to cause AC signals on the first node and the second node to flow to the sensor;
   the voltage comparison circuit is connected to the first node, a reference voltage end, and an output end, and is configured to compare voltages of the first node and the reference voltage end; and to output a first control signal through the output end when the voltage of the first node is smaller than the voltage of the reference voltage end, and to output a second control signal through the output end when the voltage of the first node is larger than the voltage of the reference voltage end.

2. The control circuit for a wearable device according to claim 1, wherein the power supply circuit comprises a first power supply sub-circuit and a second power supply sub-circuit;
   the first power supply circuit is connected to the high voltage end, the first signal input end, and the first node;
   the second power supply circuit is connected to the low voltage end, the second signal input end, and the second node.

3. The control circuit for a wearable device according to claim 1, wherein the DC blocking circuit comprises a first DC blocking sub-circuit and a second DC blocking sub-circuit;
   the first DC blocking sub-circuit is connected to the first node and the sensor;
   the second DC blocking sub-circuit is connected to the second node and the sensor.

4. The control circuit for a wearable device according to claim 2, wherein the first power supply sub-circuit comprises a first resistor, and the second power supply sub-circuit comprises a second resistor;
   a first end of the first resistor is connected to the high voltage end, and a second end of the first resistor is connected to the first node and the first signal input end;
   a first end of the second resistor is connected to the low voltage end, and a second end of the second resistor is connected to the second node and the second signal input end.

5. The control circuit for a wearable device according to claim 3, wherein the first DC blocking sub-circuit comprises a first capacitor, and the second DC blocking sub-circuit comprises a second capacitor;
   a first end of the first capacitor is connected to the first node, and a second end of the first capacitor is connected to the sensor;
   a first end of the second capacitor is connected to the second node, and a second end of the second capacitor is connected to the sensor.

6. The control circuit for a wearable device according to claim 1, further comprising a voltage follower, wherein an input end of the voltage follower is connected to the first node, and an output end of the voltage follower is connected to the voltage comparison circuit and is configured to amplify a DC signal on the first node and to keep the voltage unchanged.

7. The control circuit for a wearable device according to claim 1, wherein the sensor is configured to collect at least one of electrocardiogram data, respiratory data, sleep data, and exercise data.

8. A wearable device, comprising a control circuit for a wearable device, a communication module, and a power management module,
   wherein the control circuit comprises: a power supply circuit, a DC blocking circuit, and a voltage comparison circuit,
   wherein the power supply circuit is connected to a high voltage end, a low voltage end, a first signal input end, a second signal input end, a first node, and a second node; the power supply circuit is configured to output a voltage of the first signal input end to the first node and to output a voltage of the second signal input end to the second node according to voltages supplied by the high voltage end and the low voltage end;
   the DC blocking circuit is connected to the first node, the second node, and a sensor in the wearable device, and is configured to block DC signals on the first node and the second node from flowing to the sensor, and to cause AC signals on the first node and the second node to flow to the sensor;
   the voltage comparison circuit is connected to the first node, a reference voltage end, and an output end, and is configured to compare voltages of the first node and the reference voltage end; and to output a first control signal through the output end when the voltage of the first node is smaller than the voltage of the reference voltage end, and to output a second control signal through the output end when the voltage of the first node is larger than the voltage of the reference voltage end,
   wherein an output end of the voltage comparison circuit in the control circuit is connected to a power management module, and the power management module is connected to the communication module;
   the power management module is configured to convert the communication module from a sleep state to an operating state according to the first control signal output by the voltage comparison circuit; and is further configured to convert the communication module from the operating state to the sleep state according to the second control signal output by the voltage comparison circuit.

9. The wearable device according to claim 8, further comprising a processor and a memory,
wherein the processor is configured to receive data collected by the sensor and to store the data in the memory.

10. The wearable device according to claim 8, wherein the communication module is a Bluetooth module or a Wi-Fi module, or a Zigbee module.

11. The wearable device according to claim 8, wherein the power supply circuit comprises a first power supply sub-circuit and a second power supply sub-circuit;
the first power supply circuit is connected to the high voltage end, the first signal input end, and the first node;
the second power supply circuit is connected to the low voltage end, the second signal input end, and the second node.

12. The wearable device according to claim 8, wherein the DC blocking circuit comprises a first DC blocking sub-circuit and a second DC blocking sub-circuit;
the first DC blocking sub-circuit is connected to the first node and the sensor;
the second DC blocking sub-circuit is connected to the second node and the sensor.

13. The wearable device according to claim 11, wherein the first power supply sub-circuit comprises a first resistor, and the second power supply sub-circuit comprises a second resistor;
a first end of the first resistor is connected to the high voltage end, and a second end of the first resistor is connected to the first node and the first signal input end;
a first end of the second resistor is connected to the low voltage end, and a second end of the second resistor is connected to the second node and the second signal input end.

14. The wearable device according to claim 12, wherein the first DC blocking sub-circuit comprises a first capacitor, and the second DC blocking sub-circuit comprises a second capacitor;
a first end of the first capacitor is connected to the first node, and a second end of the first capacitor is connected to the sensor;
a first end of the second capacitor is connected to the second node, and a second end of the second capacitor is connected to the sensor.

15. The wearable device according to claim 8, further comprising a voltage follower, wherein an input end of the voltage follower is connected to the first node, and an output end of the voltage follower is connected to the voltage comparison circuit and is configured to amplify a DC signal on the first node and to keep the voltage unchanged.

16. The wearable device according to claim 8, wherein the sensor is configured to collect at least one of electrocardiogram data, respiratory data, sleep data, and exercise data.

* * * * *